(12) United States Patent
Wang

(10) Patent No.: US 6,780,969 B2
(45) Date of Patent: Aug. 24, 2004

(54) SYNTHETIC PEPTIDE COMPOSITION AS IMMUNOGENS FOR PREVENTION OF URINARY TRACT INFECTION

(75) Inventor: Chang Yi Wang, Cold Spring Harbor, NY (US)

(73) Assignee: United Biomedical, Inc., Hauppauge, NY (US)

( * ) Notice: Subject to any disclaimer, the term of this patent is extended or adjusted under 35 U.S.C. 154(b) by 50 days.

(21) Appl. No.: 09/747,802

(22) Filed: Dec. 22, 2000

(65) Prior Publication Data

US 2003/0027979 A1 Feb. 6, 2003

(51) Int. Cl.$^7$ .................... A61K 38/00; A61K 39/00; A61K 38/24; C07K 1/00
(52) U.S. Cl. ................ 530/324; 424/198.1; 530/313; 530/326; 530/350
(58) Field of Search .................. 530/350, 324, 530/313, 326; 424/198.1

(56) References Cited

U.S. PATENT DOCUMENTS

| | | | |
|---|---|---|---|
| 4,454,114 A | | 6/1984 | Strasilla et al. |
| 4,740,585 A | | 4/1988 | Schmidt et al. |
| 5,759,551 A | | 6/1998 | Ladd et al. |
| 6,025,468 A | * | 2/2000 | Wang .................. 530/324 |

FOREIGN PATENT DOCUMENTS

WO    WO 95/11998    5/1995    ............ C12Q/1/70

OTHER PUBLICATIONS

Sokurenko et al, Journal of Bacteriology, Feb. 1994, 176(3):748–755.*
Harris et al, Journal of Bacteriology, Nov. 1990, pp. 6411–6418.*
Daly et al, Biochemistry, Aug. 10, 1999, 38(32):10606–10614.*
Iwai et al (FEBS Letter, Oct. 8, 1999, 459(2):166–172.*
Abraham et al, Nature, 1988, vol. 326, p. 682–684.*
Schutze et al, Journal of Immunology, 1985, 2319–2322.*
Hamrick et al, Journal of Bacteriology, Jul. 2000, pp. 4012–4021.
Schembri et al, Infection and Immunity, May 2000, pp. 2638–2646.
Langermann et al, Science, vol. 276, Apr. 25, 1997.
Seqeuence alignment of SEQ ID No:5 and sequence from Klemm et al.*
Sequence alignment of SEQ ID NO:5 and sequence from Sokurenko et al.*
Service, Science, vol. 276, p. 533, 1997.
Hanson et al., Nature, vol. 332, pp. 265–268, 1988.
Johnson, Clin. Microbiology Reviews, vol. 4:1, pp. 80–128, 1991.
Langermann et al., Science, vol. 276, pp. 607–611, 1997.
Schmidt et al., J. of Experimental Medicine, vol. 161, pp. 705–717, 1984.
Abraham, Nature, vol. 336, pp. 682–684, 1988.
Klemm et al., Mol. Gen. Genet., vol. 208, pp. 439–445, 1987.
Abraham et al., J. of Bacteriology, vol. 169:12, pp. 5530–5536, 1987.
Jones et al., Proc. Natl. Acad. Sci., vol. 92, pp. 2081–2085, 1995.
Thankavel et al., J. Clin. Invest., vol. 100:5, pp. 1123–1136, 1997.
Choudhury et al., Science, vol. 285, pp. 1061–1066, 1999.
Langermann et al., J. of Infectious Diseases vol. 181, pp. 774–778, 2000.
Marie–Paule Schutze et al., J. of Immunol., vol. 135:4, pp. 2319–2322, 1985.
Babbit et al., Nature, vol. 317, pp. 359–361, 1985.
Cease et al., Proc. Natl. Acad. Sci., vol. 84, pp. 4249–4253, 1987.
Partidos et al., J. of Gen. Virol., vol. 72, pp. 1293–1299, 1991.
Meister et al., Vaccine, vol. 13:6, pp. 581–591, 1995.

* cited by examiner

Primary Examiner—Lynette R. F. Smith
Assistant Examiner—Vanessa L. Ford
(74) Attorney, Agent, or Firm—Morgan & Finnegan, LLP

(57) ABSTRACT

The invention provides a peptide immunogen comprising a FAFSD target peptide or an anlogue thereof, covalently linked to a helper T cell epitope and optionally to an invasin immunostimulatory domain. The present invention also provides for the use of such peptide immunogens to elicit the production in mammals of high titer polyclonal antibodies, which are specific to the FAFSD target peptide. The peptide immunogens are expected to be useful in evoking antibodies that prevent the adherence of E. coli and other enterobacteria to the bladder mucosa for protection against urinary tract infection.

28 Claims, 1 Drawing Sheet

Title: Synthetic Peptide Composition as Immunogens for Prevention of Urinary Tract Infection Inventor: Chang Yi Wang Serial No. : 09/747,802

SEQUENCE LISTING

<160> NUMBER OF SEQ ID NOS: 88

<210> SEQ ID NO 1
<211> LENGTH: 268
<212> TYPE: PRT
<213> ORGANISM: Escherichia coli

<400> SEQUENCE: 1

Phe Ala Cys Lys Thr Ala Asn Gly Thr Ala Ile Pro Ile Gly Gly Gly
 1               5                  10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

Asp Ser Ala Arg Asp Val Thr Pro Asp Tyr Pro Gly Ser Val Pro Thr

```
                165                 170                 175
Pro Leu Thr Val Tyr Ala Lys Ser Gln Asn Leu Gly Tyr Tyr Leu Ser
            180                 185                 190
Thr Thr Ala Ala Gly Asn Ser Ile Phe Thr Asn Thr Ala Ser Phe Ser
        195                 200                 205
Pro Ala Gln Gly Val Gly Val Gln Leu Thr Arg Asn Gly Thr Ile Ile
    210                 215                 220
Pro Ala Asn Asn Thr Val Ser Leu Gly Ala Val Gly Thr Ser Ala Val
225                 230                 235                 240
Ser Leu Gly Leu Thr Ala Asn Tyr Ala Arg Thr Gly Gly Gln Val Ala
                245                 250                 255
Asn Val Gln Ser Ile Ile Gly Val Thr Phe Val Gln
            260                 265

<210> SEQ ID NO 2
<211> LENGTH: 27
<212> TYPE: PRT
<213> ORGANISM: Escherichia coli

<400> SEQUENCE: 2

Cys Lys Ile Ala Asn Gly Ile Ala Ile Pro Ile Gly Gly Gly Ser Ala
  1               5                  10                  15

Asn Val Tyr Val Asn Leu Ala Pro Val Val Cys
            20                  25

<210> SEQ ID NO 3
<211> LENGTH: 25
<212> TYPE: PRT
<213> ORGANISM: Escherichia coli

<400> SEQUENCE: 3

Phe Ala Cys Lys Thr Ala Asn Gly Thr Ala Ile Pro Ile Gly Gly Glu
  1               5                  10                  15

Ser Ala Asn Val Tyr Val Asn Leu Ala
            20                  25

<210> SEQ ID NO 4
<211> LENGTH: 25
<212> TYPE: PRT
<213> ORGANISM: Escherichia coli

<400> SEQUENCE: 4

Phe Ala Ser Lys Thr Leu Asn Gly Thr Ala Ile Pro Ile Gly Glu Gly
  1               5                  10                  15

Ser Ala Asn Cys Tyr Val Asn Leu Ala
            20                  25

<210> SEQ ID NO 5
<211> LENGTH: 13
<212> TYPE: PRT
<213> ORGANISM: Escherichia coli

<400> SEQUENCE: 5

Cys Ala Ser Lys Thr Ala Asn Gly Thr Ala Ile Pro Cys
  1               5                  10

<210> SEQ ID NO 6
<211> LENGTH: 9
<212> TYPE: PRT
<213> ORGANISM: Escherichia coli
```

```
<400> SEQUENCE: 6

Cys Asp Tyr Pro Glu Thr Ile Thr Cys
  1               5

<210> SEQ ID NO 7
<211> LENGTH: 11
<212> TYPE: PRT
<213> ORGANISM: Escherichia coli

<400> SEQUENCE: 7

Cys Asn Asp Tyr Pro Glu Thr Ile Thr Asp Cys
  1               5                  10

<210> SEQ ID NO 8
<211> LENGTH: 18
<212> TYPE: PRT
<213> ORGANISM: Escherichia coli

<400> SEQUENCE: 8

Cys Ile Leu Arg Gln Thr Asn Asn Tyr Asn Ser Asp Asp Phe Gln Phe
  1               5                  10                  15

Val Leu

<210> SEQ ID NO 9
<211> LENGTH: 15
<212> TYPE: PRT
<213> ORGANISM: Hepatitis B virus

<400> SEQUENCE: 9

Phe Phe Leu Leu Thr Arg Ile Leu Thr Ile Pro Gln Ser Leu Asp
  1               5                  10                  15

<210> SEQ ID NO 10
<211> LENGTH: 30
<212> TYPE: PRT
<213> ORGANISM: Bordetella pertussis

<400> SEQUENCE: 10

Lys Lys Leu Arg Arg Leu Leu Tyr Met Ile Tyr Met Ser Gly Leu Ala
  1               5                  10                  15

Val Arg Val His Val Ser Lys Glu Glu Gln Tyr Tyr Asp Tyr
                 20                  25                  30

<210> SEQ ID NO 11
<211> LENGTH: 17
<212> TYPE: PRT
<213> ORGANISM: Clostridium tetani

<400> SEQUENCE: 11

Lys Lys Gln Thr Ile Lys Ala Asn Ser Lys Phe Ile Gly Ile Thr Glu
  1               5                  10                  15

Leu

<210> SEQ ID NO 12
<211> LENGTH: 22
<212> TYPE: PRT
<213> ORGANISM: Clostridium tetani

<400> SEQUENCE: 12

Lys Lys Phe Asn Asn Phe Thr Val Ser Pro Tyr Leu Arg Val Pro Lys
  1               5                  10                  15

Val Ser Ala Ser His Leu
```

<210> SEQ ID NO 13
<211> LENGTH: 15
<212> TYPE: PRT
<213> ORGANISM: Bordetella pertussis

<400> SEQUENCE: 13

Tyr Met Ser Gly Leu Ala Val Arg Val His Val Ser Lys Glu Glu
 1               5                  10                  15

<210> SEQ ID NO 14
<211> LENGTH: 27
<212> TYPE: PRT
<213> ORGANISM: Clostridium tetani

<400> SEQUENCE: 14

Tyr Asp Pro Asn Tyr Leu Arg Thr Asp Ser Asp Lys Asp Arg Phe Leu
 1               5                  10                  15

Gln Thr Met Val Lys Leu Phe Asn Arg Ile Lys
             20                  25

<210> SEQ ID NO 15
<211> LENGTH: 24
<212> TYPE: PRT
<213> ORGANISM: Bordetella pertussis

<400> SEQUENCE: 15

Gly Ala Tyr Ala Arg Cys Pro Asn Gly Thr Arg Ala Leu Thr Val Ala
 1               5                  10                  15

Glu Leu Arg Gly Asn Ala Glu Leu
             20

<210> SEQ ID NO 16
<211> LENGTH: 15
<212> TYPE: PRT
<213> ORGANISM: Measles virus

<400> SEQUENCE: 16

Leu Ser Glu Ile Lys Gly Val Ile Val His Arg Leu Glu Gly Val
 1               5                  10                  15

<210> SEQ ID NO 17
<211> LENGTH: 20
<212> TYPE: PRT
<213> ORGANISM: Measles virus

<400> SEQUENCE: 17

Gly Ile Leu Glu Ser Arg Gly Ile Lys Ala Arg Ile Arg His Val Asp
 1               5                  10                  15

Thr Glu Ser Thr
             20

<210> SEQ ID NO 18
<211> LENGTH: 17
<212> TYPE: PRT
<213> ORGANISM: Clostridium tetani

<400> SEQUENCE: 18

Trp Val Arg Asp Ile Ile Asp Asp Phe Thr Asp Glu Ser Ser Gln Lys
 1               5                  10                  15

Thr

<210> SEQ ID NO 19
<211> LENGTH: 16
<212> TYPE: PRT
<213> ORGANISM: Clostridium tetani

<400> SEQUENCE: 19

```
Asp Val Ser Thr Ile Val Pro Tyr Ile Gly Pro Ala Leu Asn His Val
  1               5                  10                  15
```

<210> SEQ ID NO 20
<211> LENGTH: 25
<212> TYPE: PRT
<213> ORGANISM: Chlamydia trachomatis

<400> SEQUENCE: 20

```
Ala Leu Asn Ile Trp Asp Arg Phe Asp Val Phe Cys Thr Leu Gly Ala
  1               5                  10                  15

Thr Thr Gly Tyr Leu Lys Gly Asn Ser
             20                  25
```

<210> SEQ ID NO 21
<211> LENGTH: 23
<212> TYPE: PRT
<213> ORGANISM: Corynebacterium diphtheriae virus

<400> SEQUENCE: 21

```
Asp Ser Glu Thr Ala Asp Asn Leu Glu Lys Thr Val Ala Ala Leu Ser
  1               5                  10                  15

Ile Leu Pro Gly His Gly Cys
             20
```

<210> SEQ ID NO 22
<211> LENGTH: 39
<212> TYPE: PRT
<213> ORGANISM: Corynebacterium diphtheriae virus

<400> SEQUENCE: 22

```
Glu Glu Ile Val Ala Gln Ser Ile Ala Leu Ser Ser Leu Met Val Ala
  1               5                  10                  15

Gln Ala Ile Pro Leu Val Gly Glu Leu Val Asp Ile Gly Phe Ala Arg
             20                  25                  30

Thr Asn Phe Val Glu Ser Cys
         35
```

<210> SEQ ID NO 23
<211> LENGTH: 21
<212> TYPE: PRT
<213> ORGANISM: Plasmodium falciparum

<400> SEQUENCE: 23

```
Asp His Glu Lys Lys His Ala Lys Met Glu Lys Ala Ser Ser Val Phe
  1               5                  10                  15

Asn Val Val Asn Ser
             20
```

<210> SEQ ID NO 24
<211> LENGTH: 17
<212> TYPE: PRT
<213> ORGANISM: Schistosoma mansoni

<400> SEQUENCE: 24

```
Lys Trp Phe Lys Thr Asn Ala Pro Asn Gly Val Asp Glu Lys His Arg
```

-continued

```
                1               5                  10                 15
His

<210> SEQ ID NO 25
<211> LENGTH: 14
<212> TYPE: PRT
<213> ORGANISM: Escherichia coli

<400> SEQUENCE: 25

Gly Leu Gln Gly Lys His Ala Asp Ala Val Lys Ala Lys Gly
  1               5                  10

<210> SEQ ID NO 26
<211> LENGTH: 19
<212> TYPE: PRT
<213> ORGANISM: Escherichia coli

<400> SEQUENCE: 26

Gly Leu Ala Ala Gly Leu Val Gly Met Ala Ala Asp Ala Met Val Glu
  1               5                  10                 15

Asp Val Asn

<210> SEQ ID NO 27
<211> LENGTH: 20
<212> TYPE: PRT
<213> ORGANISM: Escherichia coli

<400> SEQUENCE: 27

Ser Thr Glu Thr Gly Asp Gln His His Tyr Gln Thr Arg Val Val Ser
  1               5                  10                 15

Asn Ala Asn Lys
            20

<210> SEQ ID NO 28
<211> LENGTH: 20
<212> TYPE: PRT
<213> ORGANISM: Hepatitis B virus

<400> SEQUENCE: 28

Ser Asp Phe Phe Pro Ser Val Arg Asp Leu Leu Asp Thr Ala Ser Ala
  1               5                  10                 15

Leu Tyr Arg Glu
            20

<210> SEQ ID NO 29
<211> LENGTH: 12
<212> TYPE: PRT
<213> ORGANISM: Chlamydia trachomatis

<400> SEQUENCE: 29

Thr Ile Asn Lys Pro Lys Gly Tyr Val Gly Lys Glu
  1               5                  10

<210> SEQ ID NO 30
<211> LENGTH: 15
<212> TYPE: PRT
<213> ORGANISM: Measles virus

<400> SEQUENCE: 30

Leu Ser Glu Ile Lys Gly Val Ile Val His Arg Leu Glu Gly Val
  1               5                  10                 15
```

```
<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 31

Asp Leu Ser Asp Leu Lys Gly Leu Leu Leu His Lys Leu Asp Gly Leu
  1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 32

Glu Ile Ser Glu Ile Arg Gly Ile Ile Ile His Arg Ile Glu Gly Ile
  1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 33

Asp Val Ser Asp Val Lys Gly Val Val Val His Lys Val Asp Gly Val
  1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 34

Asp Phe Ser Asp Phe Lys Gly Phe Phe Phe His Lys Phe Asp Gly Phe
  1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 35

Ile Ser Glu Ile Lys Gly Val Ile Val His Lys Ile Glu Gly Ile
  1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 36
```

```
Met Thr Glu Ile Arg Thr Val Ile Val Thr Arg Met Glu Thr Met
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 37

Leu Ser Glu Ile Lys Gly Val Ile Val His Lys Leu Glu Gly Val
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 38

Ile Ser Glu Ile Lys Gly Val Ile Val His Lys Ile Glu Gly Ile
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 39

Ile Thr Glu Ile Arg Thr Val Ile Val Thr Arg Ile Glu Thr Ile
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 40

Met Ser Glu Ile Lys Gly Val Ile Val His Lys Leu Glu Gly Met
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 41

Leu Thr Glu Met Arg Thr Val Ile Val Thr Arg Met Glu Thr Val
 1               5                  10                  15

<210> SEQ ID NO 42
<211> LENGTH: 15
<212> TYPE: PRT
<213> ORGANISM: Artificial Sequence
```

-continued

```
<220> FEATURE:
<223> OTHER INFORMATION: Description of Artificial Sequence:  T HELPER
      SEQUENCE DERIVED FROM MEASLES VIRUS

<400> SEQUENCE: 42

Ile Ser Glu Ile Lys Gly Val Ile Val His L

Met Leu Phe

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM MEASLES VIRUS

<400> SEQUENCE: 48

Ile Ser Leu Ser Glu Ile Lys Gly Val Ile Val His Lys Leu Glu Gly
 1               5                  10                  15

Val Leu Phe

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM MEASLES VIRUS

<400> SEQUENCE: 49

Ile Ser Ile Ser Glu Ile Lys Gly Val Ile Val His Lys Ile Glu Gly
 1               5                  10                  15

Ile Leu Phe

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM MEASLES VIRUS

<400> SEQUENCE: 50

Ile Ser Ile Thr Glu Ile Arg Thr Val Ile Val Thr Arg Ile Glu Thr
 1               5                  10                  15
Ile Leu Phe

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM MEASLES VIRUS

<400> SEQUENCE: 51

Ile Ser Leu Ser Glu Ile Lys Gly Val Ile Val His Lys Leu Glu Gly
 1               5                  10                  15

Met Leu Phe

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM MEASLES VIRUS

<400> SEQUENCE: 52

Ile Ser Met Thr Glu Met Arg Thr Val Ile Val Thr Arg Met Glu Thr
 1               5                  10                  15

Val Leu Phe

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 53

Ile Ser Leu Thr Glu Ile Arg Thr Val Ile Val Thr Arg Leu Glu Thr
 1               5                  10                  15

Val Leu Phe

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 54

Ile Ser Ile Thr Glu Ile Arg Thr Val Ile Val Thr Arg Ile Glu Thr
 1               5                  10                  15

Ile Leu Phe

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 55

Ile Ser Ile Ser Glu Ile Lys Gly Val Ile Val His Lys Ile Glu Gly
 1               5                  10                  15

Ile Leu Phe

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 56

Ile Ser Ile Thr Glu Ile Arg Thr Val Ile Val Thr Arg Ile Glu Thr
 1               5                  10                  15

Ile Leu Phe

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS

<400> SEQUENCE: 57

Ile Ser Met Ser Glu Met Lys Gly Val Ile Val His Lys Met Glu Gly
 1               5                  10                  15

Met Leu Phe

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM MEASLES VIRUS

<400> SEQUENCE: 58

Ile Ser Leu Thr Glu Ile Arg Thr Val Ile Val Thr Arg Leu Glu Thr
 1               5                  10                  15

Val Leu Phe

<210> SEQ ID NO 59
<211> LENGTH: 15
<212> TYPE: PRT
<213> ORGANISM: Hepatitis B virus

<400> SEQUENCE: 59

Phe Phe Leu Leu Thr Arg Ile Leu Thr Ile Pro Gln Ser Leu Asp
 1               5                  10                  15

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM HEPATITIS B VIRUS

<400> SEQUENCE: 60

Lys Lys Lys Phe Phe Leu Leu Thr Arg Ile Leu Thr Ile Pro Gln Ser
 1               5                  10                  15

Leu Asp

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM HEPATITIS B VIRUS

<400> SEQUENCE: 61

Phe Phe Leu Leu Thr Arg Ile Leu Thr Ile Pro Gln Ser Leu
 1               5                  10

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: T HELPER
      SEQUENCE DERIVED FROM HEPATITIS B VIRUS

<400> SEQUENCE: 62

Lys Lys Lys Leu Phe Leu Leu Thr Lys Leu Leu Thr Leu Pro Gln Ser
 1               5                  10                  15

Leu Asp

<210> SEQ ID NO 63
<211> LENGTH: 18

```
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 63

Arg Arg Arg Ile Leu Ile Ile Thr Arg Ile Ile Thr Ile Pro Leu Ser
 1               5                  10                  15

Ile Arg

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 64

Lys Lys Lys Val Arg Val Val Thr Lys Val Val Thr Val Pro Ile Ser
 1               5                  10                  15

Val Asp

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 65

Lys Lys Lys Phe Phe Phe Phe Thr Lys Phe Phe Thr Phe Pro Val Ser
 1               5                  10                  15

Phe Asp

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 66

Lys Lys Lys Leu Phe Leu Leu Thr Lys Leu Leu Thr Leu Pro Phe Ser
 1               5                  10                  15

Leu Asp

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 67

Lys Lys Lys Ile Ile Thr Ile Thr Arg Ile Ile Thr Ile Ile Thr Thr
 1               5                  10                  15

Ile Asp
```

-continued

```
<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 68

Lys Lys Lys Ile Ile Thr Ile Thr Arg Ile Ile Thr Ile Ile Thr Thr
  1               5                  10                  15

Ile

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 69

Lys Lys Lys Met Met Thr Met Thr Arg Met Ile Thr Met Ile Thr Thr
  1               5                  10                  15

Ile Asp

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 70

Phe Ile Thr Met Asp Thr Lys Phe Leu Leu Ala Ser Thr His Ile Leu
  1               5                  10                  15

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM HEPATITIS B VIRUS

<400> SEQUENCE: 71

Lys Lys Lys Phe Ile Thr Met Asp Thr Lys Phe Leu Leu Ala Ser Thr
  1               5                  10                  15

His Ile Leu

<210> SEQ ID NO 72
<211> LENGTH: 16
<212> TYPE: PRT
<213> ORGANISM: Yersinia pseudotuberculosis

<400> SEQUENCE: 72

Thr Ala Lys Ser Lys Lys Phe Pro Ser Tyr Thr Ala Thr Tyr Gln Phe
  1               5                  10                  15

<210> SEQ ID NO 73
<211> LENGTH: 6
<212> TYPE: PRT
<213> ORGANISM: Homo sapiens

<400> SEQUENCE: 73

```
Pro Pro Asp Pro Asp Pro
 1               5
```

<210> SEQ ID NO 74
<211> LENGTH: 46
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 74

```
Ile Ser Ile Ser Glu Ile Lys Gly Val Ile Val His Lys Ile Glu Gly
 1               5                  10                  15

Ile Leu Phe Gly Gly Phe Ala Cys Lys Thr Ala Asn Gly Thr Ala Ile
            20                  25                  30

Pro Ile Gly Gly Gly Ser Ala Asn Val Tyr Val Asn Leu Ala
        35                  40                  45
```

<210> SEQ ID NO 75
<211> LENGTH: 46
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 75

```
Ile Ser Ile Thr Glu Ile Arg Thr Val Ile Val Thr Arg Ile Glu Thr
 1               5                  10                  15

Ile Leu Phe Gly Gly Phe Ala Cys Lys Thr Ala Asn Gly Thr Ala Ile
            20                  25                  30

Pro Ile Gly Gly Gly Ser Ala Asn Val Thr Val Asn Leu Ala
        35                  40                  45
```

<210> SEQ ID NO 76
<211> LENGTH: 46
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 76

```
Ile Ser Ile Ser Glu Ile Lys Gly Val Ile Val His Lys Ile Glu Gly
 1               5                  10                  15

Ile Leu Phe Gly Gly Phe Ala Ser Lys Thr Cys Asn Gly Thr Ala Ile
            20                  25                  30

Pro Ile Gly Gly Gly Ser Ala Asn Cys Tyr Val Asn Leu Ala
        35                  40                  45
```

<210> SEQ ID NO 77
<211> LENGTH: 46
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 77

```
Ile Ser Ile Thr Glu Ile Arg Thr Val Ile Val Thr Arg Ile Glu Thr
 1               5                  10                  15

Ile Leu Phe Gly Gly Phe Ala Ser Lys Thr Cys Asn Gly Thr Ala Ile
```

-continued

```
                    20                  25                  30

Pro Ile Gly Gly Gly Ser Ala Asn Cys Tyr Val Asn Leu Ala
            35                  40                  45

<210> SEQ ID NO 78
<211> LENGTH: 34
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 78

Ile Ser Ile Ser Glu Ile Lys Gly Val Ile Val His Lys Ile Glu Gly
  1               5                  10                  15

Ile Leu Phe Gly Gly Cys Ala Ser Lys Thr Ala Asn Gly Thr Ala Ile
             20                  25                  30

Pro Cys

<210> SEQ ID NO 79
<211> LENGTH: 34
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 79

Ile Ser Ile Thr Glu Ile Arg Thr Val Ile Val Thr Arg Ile Glu Thr
  1               5                  10                  15

Ile Leu Phe Gly Gly Cys Ala Ser Lys Thr Ala Asn Gly Thr Ala Ile
             20                  25                  30

Pro Cys

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 80

Ile Ser Ile Ser Glu Ile Lys Gly Val Ile Val His Lys Ile Glu Gly
  1               5                  10                  15

Ile Leu Phe Gly Gly Cys Asp Tyr Pro Glu Thr Ile Thr Cys
             20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 81

Ile Ser Ile Thr Glu Ile Arg Thr Val Ile Val Thr Arg Ile Glu Thr
  1               5                  10                  15

Ile Leu Phe Gly Gly Cys Asp Tyr Pro Glu Thr Ile Thr Cys
             20                  25                  30

<210> SEQ ID NO 82
```

```
<211> LENGTH: 32
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 82

Ile Ser Ile Ser Glu Ile Lys Gly Val Ile Val His Lys Ile Glu Gly
  1               5                  10                  15

Ile Leu Phe Gly Gly Cys Asn Asp Tyr Pro Glu Thr Ile Thr Asp Cys
             20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 83

Ile Ser Ile Thr Glu Ile Arg Thr Val Ile Val Thr Arg Ile Glu Thr
  1               5                  10                  15

Ile Leu Phe Gly Gly Cys Asn Asp Tyr Pro Glu Thr Ile Thr Asp Cys
             20                  25                  30

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 84

Ile Ser Ile Ser Glu Ile Lys Gly Val Ile Val His Lys Ile Glu Gly
  1               5                  10                  15

Ile Leu Phe Gly Gly Cys Ile Leu Arg Gln Thr Asn Asn Thr Asn Ser
             20                  25                  30

Asp Asp Phe Gln Phe Val Cys
         35

<210> SEQ ID NO 85
<211> LENGTH: 39
<212> TYPE: PRT
<213> ORGANISM: Artificial Sequence
<220> FEATURE:
<223> OTHER INFORMATION: Description of Artificial Sequence:  T HELPER
      SEQUENCE DERIVED FROM MEASLES VIRUS AND E. COLI

<400> SEQUENCE: 85

Ile Ser Ile Thr Glu Ile Arg Thr Val Ile Val Thr Arg Ile Glu Thr
  1               5                  10                  15

Ile Leu Phe Gly Gly Cys Ile Leu Arg Gln Thr Asn Asn Tyr Asn Ser
             20                  25                  30

Asp Asp Phe Gln Phe Val Cys
         35

<210> SEQ ID NO 86
<211> LENGTH: 10
<212> TYPE: PRT
<213> ORGANISM: Escherichia coli

<400> SEQUENCE: 86
```

```
Cys Glu Asp Tyr Pro Asp Thr Ile Thr Cys
 1               5                  10

<210> SEQ ID NO 87
<211> LENGTH: 12
<212> TYPE: PRT
<213> ORGANISM: Escherichia coli

<400> SEQUENCE: 87

Cys Asn Asp Tyr Pro Glu Thr Ile Thr Asp Ala Cys
 1               5                  10

<210> SEQ ID NO 88
<211> LENGTH: 21
<212> TYPE: PRT
<213> ORGANISM: Escherichia coli

<400> SEQUENCE: 88

Thr Gln Ile Phe Cys His Asn Asp Tyr Pro Glu Thr Ile Thr Asp Cys
 1               5                  10                  15

Tyr Val Asp Leu Ala
                20
```

SYNTHETIC PEPTIDE COMPOSITION AS IMMUNOGENS FOR PREVENTION OF URINARY TRACT INFECTION

FIELD OF THE INVENTION

This invention relates to peptide compositions that are useful as immunogens for the prevention of urinary tract infection. The peptide immunogen of the present invention comprises a FimH Adhesin Functional Site-Derived (FAFSD) target peptide and a helper T cell epitope (Th) having multiple class II MHC binding motifs. Optionally, the immunogenic peptide further comprises an invasin domain, which acts as a general immune stimulator. The helper T cell epitope and the invasin domain enable the host to generate an immune response specific against the FAFSD target peptide to prevent the adherence of *Escherichia coli* and other enterobacteria to the bladder mucosa and confer protection against urinary tract infection.

BACKGROUND OF THE INVENTION

Urinary tract infection (UTI) is one of the most common disorders in women and children, resulting in 7–8 million physician and hospital visits per year at a cost of over $1 billion. It is estimated that by age 30, roughly 50 percent of women have had at least one incidence of UTI with 2–10 percent having recurrent UTI. Females are generally more prone to UTI because of their anatomy. Recent studies have shown that, on average, women who are 18–40 years old suffer 1–2 infections over a two year period. Older women are at risk with the incidence being as high as 30%. In most cases, UTI is not life threatening. Standard antibiotics usually offer quick relief, but when left untreated, the chronic recurrence of urinary tract infection can cause kidney damage and even death. A vaccine would reduce this toll but there has been little success in the development of a practicable vaccine for UTI (Service, *Science* 1997, 276:533).

Earlier attempts to produce a UTI vaccine using whole fimbriae were not successful in protecting against a broad range of disease-causing bacteria. Intact whole fimbriae do not elicit a strong antibody response to FimH adhesin. (Hanson and Brinton, *Nature* 1988, 332:265; Johnson, 1991; U.S. Pat. No. 4,454,117, Langermann et al, 1997). Vaccines comprising peptides of the major fimbrial protein FimA have been reported (Schmidt et al, *J Exp Med*, 1985; 161:705; U.S. Pat. No. 4,740,585). However, antibodies raised against FimA are not anti-adhesive and do not block attachment. Furthermore, vaccines based on the major components of the fimbriae contain variable sites and are expected to provide a narrow typespecific protection (Abraham et al, 1988).

Certain strains of *Escherichia coli* (*E. coli*) are the main cause of UTI. While many factors contribute to the initiation and progression of UTI, it is widely accepted that attachment of bacteria to tissue in the urinary tract is a first step in the initiation of active infection. A number of studies have pointed to a role for "fimbriae" or "pilus" organelles, the long filamentous proteinaceous appendages on the surface of *E. coli*, as the primary means by which the bacteria fasten onto urogenital tissue to establish an infection. Studies have shown that an overwhelming majority of the uropathogenic *E. coli* isolates express mannose-binding type 1 fimbriae (Johnson, *Clin Microbiol Rev*, 1991; 4:80).

Specifically, a cluster of eight to nine closely associated genes located in the bacterial chromosome are responsible for the biogenesis, assembly and function of type 1 fimbriae (Klemm & Christiansen, *Mol Gen Genet*, 1987; 208:439–445). Each type 1 fimbrial filament is 1–2 μm long with a diameter of 7 nm. It is a heteropolymer comprising a major subunit FimA and three minor subunits FimF, FimG, and FimH. The FimA subunits constitute >95% of the total fimbrial proteins and are arranged in a tight right-handed helix forming a central axial hole (Klemm & Christiansen, 1987; Johnson, 1991).

More specifically, type 1 fimbriae has, as a minor component, the mannose-binding FimH adhesin which is serologically conserved throughout the Enterobacteriaceae genera (Abraham et al, *Nature*, 1988; 336:682). Immune electron microscopy has revealed FimH to be placed strategically at the distal fimbrial tips and along the fimbriae at various intervals (Abraham et al, *J Bacteriol*, 1987; 169:5530). The FimH molecules that are localized at the fimbrial tips appear to be complexed with FimG in a flexible fibrillum structure (Jones et al., *Proc Natl Acad Sci USA*, 1995; 92:2081). The presence of FimH is important for initiating bacterial infections in the urinary tract (Langermann et al, *Science*, 1997; 276:607). The mannose-binding domain of FimH is localized at the amino terminus region of FimH (Jones et al, 1995). The mannose-binding site is believed to promote attachment of the bacteria to D-mannose-containing receptors on the host mucosa cells. In fact, antibodies specific to residues of the amino terminus region of FimH inhibited attachment by type 1 fimbriated *E. coli* to human buccal cells and to the mouse bladder epithelium (Abraham et al, 1987; Thankavel et al, *J Clin Invest*, 1997; 100:1123). This indicates involvement of the mannose-binding domain of FimH in the adherence of fimbriae as a potential virulence determinant.

In light of the role played by FimH in promoting the adherence of *E. coli*, a more detailed structure-function study was conducted to map the functionally important domains within the FimH molecule. FimH is folded into two domains belonging to the all-beta class connected by a short linker. The full sequence of the FimH molecule is shown in FIG. 1. The $NH_2$-terminal mannose-binding lectin domain comprises residues 1 to156, and the COOH-terminal fimbriae domain, which anchors the adhesin to the fimbriae, comprises residues 160 to 279. The lectin domain of FimH is an 11-stranded elongated β barrel with a jellyroll-like topology. A pocket capable of accommodating a monomannose unit is located at the tip of the domain, distal from the connection to the pilin domain (Choudhury et al, *Science*, 1999; 285:1061).

The identification the tip adhesins of FimH, as a key virulence factor provided a specific target for vaccine development. In contrast to the variability of the major fimbrial protein, FimH is conserved throughout the genera of the Enterobacteriaceae. This has implications for the development of broadly protective vaccines against UTI (Abraham et al, 1988).

Recent vaccine development has been focused against the presumed FimH virulence determinant and have been more successful. Antibodies were raised in mice to two forms of FimH protein: 1) a complex containing the periplasmic chaperone FimC bound to full-length FimH protein, and 2) a naturally occurring mannose-binding FimH truncate corresponding to two-thirds of the FimH amino terminal blocked the ability of uropathogenic *E. coli* to bind to cells of a human bladder epithelial cell line, and protected mice from infection in vivo (Langermann et al, 1997). In a more recent in vivo study, a vaccine based on the FimH-FimC chaperone complex immunogen protected cynomolgus monkeys from infection by an *E. coli* cystitis isolate (Langermann et al, *J Infect Dis*, 2000; 181:774).

Thankanel et al (1997) reported that a domain localized in the FimH adhesin of *Escherichia coli* Type 1 fimbriae is capable of receptor recognition. He further reported the use of a domain specific antibody to confer protection against urinary tract infection. In that report, mice actively immunized with sFimH$_{1-25}$ peptide (see Table 3, SEQ ID NO:2) exhibited significantly lower levels of bacterial bladder colonization when challenged by type-1 fimbriated *E. coli*. As expected from the conservation of FimH sequence among type 1-fimbriated bacteria, broad immunological cross-reactivity was reported for type-1 fimbriated. Antibodies generated against a peptide-carrier protein immunogen wherein the peptide is SEQ ID NO:2 displayed significant cross-reactivity to type-1 frimbriated urinary tract isolates *Klebsiella pneumoniae* Cl111, *K. pneumoniae* Cl120, *Enterobacter aerogenes, E. coli* Cl115, *E. coli* Cl116, *E. coli* Cl118, *E. coli* Cl121, *E. coli* Cl123, *E. coli* Cl124, *E. coli* Cl5, and *Serratia marescens* Cl119 (Thankavel et al, *J Clin.Invest.*, 1997, 100:1123)

However, in Thankavel's study, the FimH adhesin peptides with built-in cysteine residues at both ends were conjugated to carrier proteins such as KLH through intermolecular crosslinking. It is known that carrier proteins are too complex for use in driving antibody responses to site-specific targets. The mass of the carrier molecule is much greater than that of the functionally important target peptide site. Consequently, the major immune response is directed to the carrier protein rather than to the target site of the peptide immunogen. Moreover, immunization with hapten-carrier conjugates frequently leads to carrier-induced immune suppression (Schutze et al., *J Immunol*, 1985, 135:2319).

Accordingly, a more suitable peptide-based is needed. It would be desirable to provide a synthetic Th-FAFSD peptide immunogen that generates a site-specific immune response without epitopic suppression by undesirable T cell responses. The peptide-based FimH immunogen should provoke an early and strong immune response in humans and animals to target FimH sites of functional importance for protective immunity without the adverse carrier-induced immune suppression. The peptide-based FimH immunogen should also be stable and well defined chemically with no need of elaborate downstream processing for ease of manufacture and quality control to avoid the need of an elaborate production plant.

Well-designed promiscuous Th/B cell epitope chimeric peptides capable of eliciting Th responses and resultant antibody responses in most members of a genetically diverse population expressing diverse MHC haplotypes have been reported. Th epitopes termed "promiscuous Th" are known to evoke efficient site-specific T cell help and can impart immunogenicity to B cell epitopes that by themselves are poorly immunogenic. Such Th epitopic peptides react with helper T-cell receptors and the class II MHC molecules, in addition to antibody binding sites (Babbitt et al., *Nature*, 1985; 317:359) to stimulate a tightly focussed site-specific antibody response to target B cell site. Promiscuous Th comprise specific sequences derived from potent immunogens including measles virus F protein and hepatitis B virus surface antigen. Many known promiscuous Th (Table 1) have been shown to be effective in potentiating a poorly immunogenic peptide corresponding to the decapeptide hormone LHRH (U.S. Pat. No. 5,759,551).

Potent Th epitopes range in size from approximately 15–30 amino acid residues in length, often share common structural features, and may contain specific landmark sequences. For example, a common feature is amphipathic helices, which are alpha-helical structures with hydrophobic amino acid residues dominating one face of the helix and with charged and polar residues dominating the surrounding faces (Cease et al., *Proc. Natl. Acad. Sci. USA*, 1987; 84: 4249). Th epitopes frequently contain additional primary amino acid patterns such as a Gly or charged residue followed by two to three hydrophobic residues, followed in turn by a charged or polar residue. This pattern defines what are called Rothbard sequences. Also, Th epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single Th epitope (Partidos et al., *J. Gen. Virol.*, 1991; 72:1293). Most, if not all, of the promiscuous T cell epitopes fit at least one of the periodicities described above.

These features may be incorporated into the designs of idealized artificial Th sites, including idealized combinatorial Th epitope libraries. For the design of combinatorial Th sites, lists of variable positions and preferred amino acids are available for MHC-binding motifs (Meister et al., *Vaccine* 1995; 13:581); and a method for producing combinatorial Th has been disclosed as structured synthetic antigen library peptides (WO 95/11998). Thus, the 1,4,5,8 rule can be applied together with combinatorial MHC-binding motifs in the assignment of positions for the invariant and degenerate sites of a combinatorial Th site and for the selection of residues for these sites, so as to vastly enlarge the range of immune responsiveness to an artificial Th. Examples of artificial idealized and idealized combinatorial library Th are shown in Table 2. See U.S. Pat. No. 6,025,468 and WO 95/11998.

TABLE 1

Pathogen-derived Promiscuous T Helper Cell Epitopes (Th)

| Description of Th | Amino Acid Sequence | SEQ ID NO |
|---|---|---|
| HBsTh[a] | FFLLTRILTIPQSLD | 9 |
| PT$_1$Th[a] | KKLRRLLYMIYMSGLAVRVHVSKEEQYYDY | 10 |
| TT$_1$Th[a] | KKQYIKANSKFIGITEL | 11 |
| TT$_2$Th[a] | KKFNNFTVSFWLRVPKVSASHL | 12 |
| PT$_{1A}$Th[a] | YMSGLAVRVHVSKEE | 13 |
| TT$_3$Th[a] | YDPNYLRTDSDKDRFLQTMVKLFNRIK | 14 |
| PT$_2$Th[a] | GAYARCPNGTRALTVAELRGNAEL | 15 |
| MV$_{F1}$Th[a] | LSEIKGVIVHRLEGV | 16 |
| MV$_{F2}$Th[a] | GILESRGI KARITHVDTESY | 17 |
| TT$_4$Th[a] | WVRDIIDDFTNESSQKT | 18 |
| TT$_5$Th[a] | DVSTIVPYIGPALNHV | 19 |
| CTT$_h$[a] | ALNIWDRFDVFCTLGATTGYLKGNS | 20 |
| DT$_1$T$_h$[a] | DSETADNLEKTVAALSILPGHGC | 21 |
| DT$_2$T$_h$[a] | EEIVAQSIALSSLMVAQAIPLVGELVDIGFAATNFVESC | 22 |
| PFT$_h$[a] | DHEKKHAKMEKASSVFNVVNS | 23 |
| SMT$_h$[a] | KWFKTNAPNGVDEKHRH | 24 |
| TraT$_1$T$_h$[a] | GLQGKHADAVKAKG | 25 |
| TraT$_2$T$_h$[a] | GLAAGLVGMAADAMVEDVN | 26 |
| TraT$_3$T$_h$[a] | STETGNQHHYQTRVVSNANK | 27 |
| HB$_{c50-69}$[b] | SDFFPSVRDLLDTASALYRE | 28 |
| CTP$_{11}$Th[c] | TINKPKGYVGKE | 29 |

[a] US 5,759,551
[b] Ferrari et al., J Clin Invest, 1991; 88:214
[c] Stagg et al., Immunology, 1993; 71:1

TABLE 2

Artificial Idealized Th and Combinatorial Library Idealized Artificial Th

| Th Identifier | Amino Acid Sequence | SEQ ID NO |
|---|---|---|
| a. MVF Th and Th epitopes derived therefrom | | |
| MVF Th1 | LSEIKGVIVHRLEGV | 30 |
| SSAL1 Th1 | DLSDLKGLLLHKLDGL | 31 |
| | EI EIR III RIE I | 32 |
| | V V VVV V V | 33 |
| | F F FFF F F | 34 |
| MVF Th1-1 | ISEIKGVIVHKIEGI | 35 |
| | MT RT TRM TM | 36 |
| | L L V | 37 |
| MVF Th1-2 | ISEIKGVIVHKIEGI | 38 |
| | T RT TR T | 39 |
| MVF Th1-3 | MSEIKGVIVHKLEGM | 40 |
| | LT MRT TRM TV | 41 |
| MVF Th1-4 | ISEIKGVIVHKIEGI | 42 |
| MVF Th1-5 | ITEIRTVIVTRIETI | 43 |
| MVF Th1-6 | MSEMKGVIVHKMEGM | 44 |
| MVF Th1-7 | LTEIRTVIVTRLETV | 45 |
| MVF Th1-8 | ISISEIKGVIVHKIEGILF | 46 |
| | MT RT TRM TM | 47 |
| | L L V | 48 |
| MVF Th1-9 | ISISEIKGVIVHKIEGILF | 49 |
| | T RT TR T | 50 |
| MVF Th1-10 | ISLSEIKGVIVHKLEGMLF | 51 |
| | MT MRT TRM TV | 52 |
| MVF Th1-11 | ISLTEIRTVIVTRLETVLF | 53 |

TABLE 2-continued

Artificial Idealized Th and Combinatorial
Library Idealized Artificial Th

| Th Identifier | Amino Acid Sequence | SEQ ID NO |
|---|---|---|
| | I           I  I | 54 |
| MVF Th1-12 | ISISEIKGVIVHKIEGILF | 55 |
| MVF Th1-13 | ISITEIRTVIVTRIETILF | 56 |
| MVF Th1-14 | ISMSEMKGVIVKMEGMLF | 57 |
| MVF Th1-15 | ISLTEIRTVIVTRLETVLF | 58 |
| b. HBsAg Th, Prototype and Derivatives | | |
| HbsAg-Th1 | FFLLTRILTIPQSLD | 59 |
| HbsAg-Th1-1 | KKKFFLLTRILTIPQSLD | 60 |
| HbsAg-Th1-2 | FFLLTFILTIPQSL | 61 |
| | KKKLFLLTKLLTLPQSLD | 62 |
| | RRRIKII RII I L IR | 63 |
| SSAL2 Th2 | VRVV  VV V I V | 64 |
| | F FF  FF F V F | 65 |
| | F | 66 |
| HbsAg-Th1-3 | KKKIITITRIITIITTID | 67 |
| HbsAg-Th1-4 | KKKIITITRIITIITTI | 68 |
| HbsAg-Th1-5 | KKKMMTMTRMITMITTID | 69 |
| HbsAg-Th1-6 | FITMDTKFLLASTHIL | 70 |
| HbsAg-Th1-7 | KKKFITMDTKFLLASTHIL | 71 |

A generalized immunostimulatory element of a domain of an invasin protein from the bacteria Yersinia spp has been reported (Brett et al., *Eur J Immunol*, 1993, 23: 1608–1614). The immune stimulatory property of invasin results from its capability to interact with the β1 integrin molecules present on T cells, particularly activated immune or memory T cells. The specific sequence for an invasin domain found to interact with the β1 integrins has been described by Brett et al (1993). A preferred embodiment of the invasin domain (Inv) for linkage to a promiscuous Th epitope has been previously described in U.S. Pat. No. 5,759,551 and is incorporated herein by reference. The said Inv domain has the sequence:

Thr-Ala-Lys-Ser-Lys-Lys-Phe-Pro-Ser-Tyr-Thr-Ala-Thr-Tyr-Gln-Phe    (SEQ ID NO:72).

To be effective, a peptide immunogen must do more than merely evoke an anti-peptide response. An effective peptide immunogen must also evoke a functional immune response, i.e., the antibody produced must have immunological cross-reactivity to the authentic target. It is known that peptide immunogens generally do not to retain a preferred structure. Therefore, it is important in designing a peptide target site to introduce structural constraints. However, the imposed structural constraint must be able to mimic the conformation of the targeted epitope so that antibodies evoked will be cross-reactivities to that site on the authentic molecule (Moore, Chapter 2 in *Synthetic Peptides A User's guide*, ed Grant, WH Freeman and Company: New York, 1992, pp 63–67).

Peptide immunogens have been designed employing promiscuous Th epitopes, the invasin domain, and with imposed structural constraint for a peptide-based vaccine for HIV (U.S. Pat. No. 6,090,388).

SUMMARY OF THE INVENTION

The present invention relates to a synthetic peptide immunogen capable of inducing antibodies against a FAFSD target peptide for the prevention of the adherence of *E. coli* and other enterobacteria to the bladder mucosa to confer protection against urinary tract infection. In particular, the peptide immunogen of this invention comprises one or more Th epitopes linked to a FAFSD target peptide, selected from the group consisting of SEQ ID NOS:3–8 and a crossreactive or immunologically functional analog of the FAFSD target peptide (Hereinafter referred to as "FAFSD peptide"). Optionally, the peptide immunogen further comprises an invasin domain (SEQ ID NO:72) as a general immune stimulator. These peptide immunogens of the present invention are effective, capable of inducing antibodies against FAFSD to prevent the adherence of *E. coli* and other enterobacteria to the bladder mucosa, thus conferring protection against urinary tract infection.

The peptide immunogen of this invention is represented by one of the following formula:

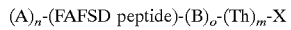

(A)$_n$-(FAFSD peptide)-(B)$_o$-(Th)$_m$-X or

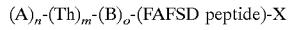

(A)$_n$-(Th)$_m$-(B)$_o$-(FAFSD peptide)-X or

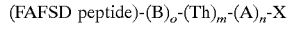

(FAFSD peptide)-(B)$_o$-(Th)$_m$-(A)$_n$-X or

(Th)$_m$-(B)$_o$-(FAFSD peptide)-(A)$_n$-X wherein each A is independently an amino acid or an invasin domain;

each B is independently an amino acid or a linking group chosen from the group consisting of an amino acid, gly-gly, (α, ε-N)lys, Pro-Pro-Xaa-Pro-Xaa-Pro (SEQ ID NO:73); NHCH(X)CH$_2$SCH$_2$CO—, —NHCH(X)CH$_2$SCH$_2$CO(ε-N)Lys-, —NHCH(X)CH$_2$S-succinimidyl(ε-N)Lys-, and —NHCH(X)CH$_2$S-(succinimidyl)-;

each Th comprise an amino acid sequence that constitutes a helper T cell epitope, or an immune enhancing analog or segment thereof;

(FAFSD peptide) is a synthetic peptide B cell target site antigen selected from the group consisting of SEQ ID NOS:2–8 or an analog thereof that is cross-reactive with and immunologically functional for FimH of fimbriae of *E. coli*;

X is an α—COOH or α—CONH₂ of an amino acid;
n is from 0 to about 10;
m is from 1 to about 4; and
o is from 0 to about 10.

Another aspect of this invention provides a vaccine comprising an immunologically effective amount of a peptide composition in accordance with this invention and one or more pharmaceutically acceptable vaccine delivery vehicles. The vaccine when administered at an appropriate dosage will generate immunotherapeutic antibodies directed against the FAFSD peptide and prevent the adherence of *E. coli* and other enterobacteria to the bladder mucosa to confer protection against urinary tract infection.

A further aspect of the invention relates to a method administering the vaccine composition to a mammal for the prevention of the adherence of *E. coli* and other enterobacteria to the bladder mucosa to confer protection against urinary tract infection in a mammal.

Generally, the synthetic immunogenic peptide, therefore, comprise about 20 to about 100 amino acids comprising the following (1) a helper T cell (Th) epitope, (2) a FAFSD peptide selected from the group consisting of SEQ ID NOS: 3–8 and an immunologically effective analogue of thereof, (3) a spacer to separate the immunogenic domains, and optionally (4) an invasin domain (SEQ ID NO:72) as a general immunostimulatory site. The Th and FAFSD peptide of the peptide immunogen are separated by a spacer comprising one or more amino acids. The optional invasin domain may be inserted in any order into the peptide provided that the immunoreactivity of the target peptide is substantially preserved or that immunoreactivity to the FAFSD target peptide is generated.

Most preferably, the peptide immunogen comprises (1) combining a FAFSD peptide with a selected promiscuous Th site to which the majority of a population of a mammal are responsive; or (2) combining a FAFSD peptide with an enlarged repertoire of Th through combinatorial chemistry to accommodate the variable immune responsiveness of a population, and (3) the stabilization of a desirable conformational feature of FAFSD peptide by cyclic constraint. Such peptide immunogens are preferred for their ability to generate a specific response to the FAFSD peptide with a broadly reactive Th response showing that the positioning of the epitopes and the cyclization is optimized.

It has been found that the peptide immunogen of the present invention, comprising a particular structural arrangement of a Th epitope alone or a Th epitope linked to an invasin domain with a target B cell site FAFSD peptide, wherein the functional site within the native structure of the FAFSD peptide is not disturbed, is effective in stimulating the production of antibodies as a vaccine against UTI.

BRIEF DESCRIPTION OF THE DRAWINGS

Figure 1:
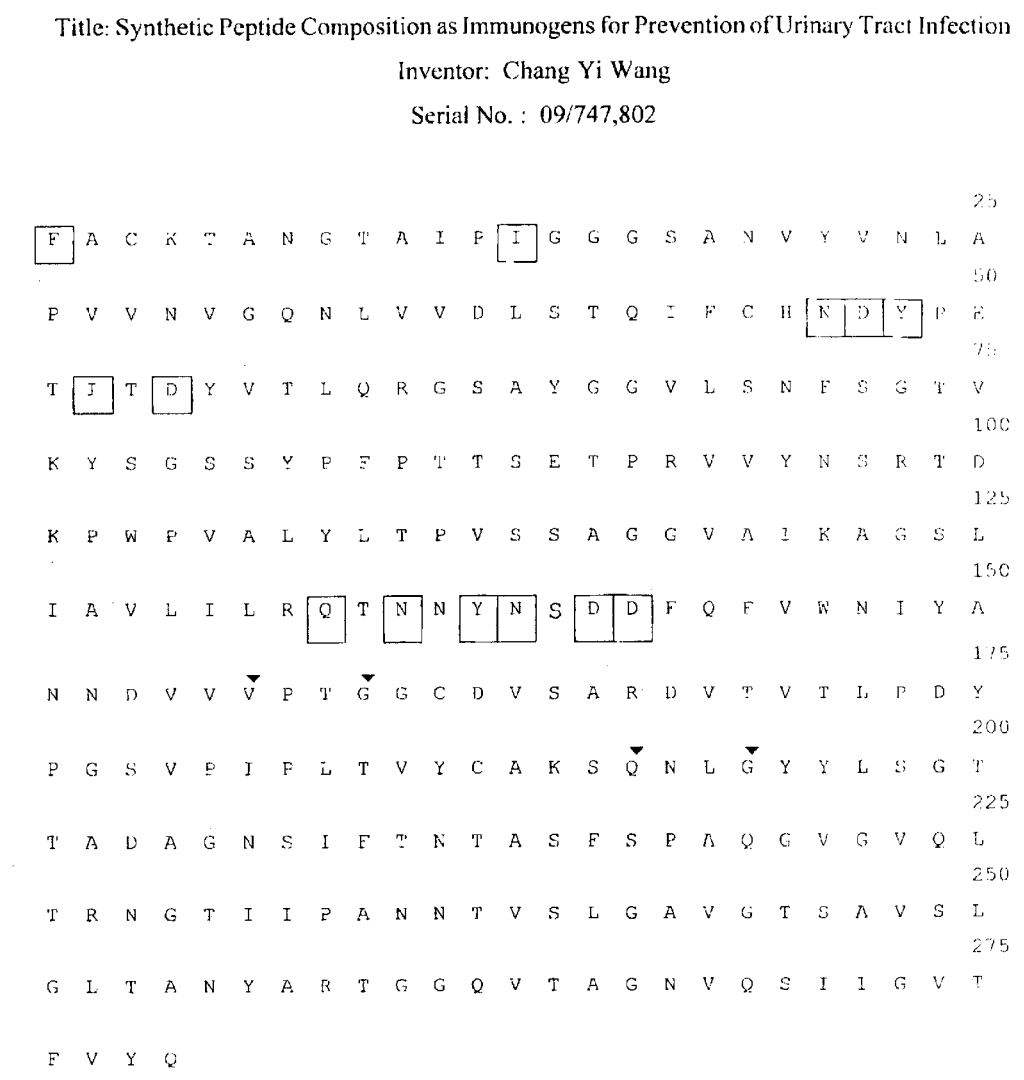

FIG. 1 is the amino acid sequence of FimH of *E. coli*. The end of the lectin domain and the start of the pilin domain are indicated by arrowheads over the amino acid positions, V and G for valine and glycine. Residue 1 of FimH is residue 22 in the precursor protein (Choudbury et al., *Science*, 1999, 285:1061). Resides that line the cabohydrate binding pocket are boxed. Abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

DETAILED DESCRIPTION OF THE INVENTION

According to the present invention a more suitable peptide-based FimH immunogen, that provokes an early and strong immune response in humans and animals to target FimH sites of functional importance for protective immunity, is provided.

The peptide based immunogen is chemically defined and is capable of eliciting a high titer of polyclonal antibodies specific for a FimH Adhesin Functional Site-Derived (FAFSD) target peptide. This is in contrast to recombinant polypeptide based vaccines (Langerman et al, 1997; 2000) and peptide-carrier conjugate vaccines (Thankanel et al, 1997). The peptide immunogen of the present has the following advantages: 1) a focused FAFSD site-specific immunity together with 2) a broad protective immunity, and 3) with less adverse side reactions than the more complex polypeptide subunit vaccines and the carrier conjugated vaccine. Moreover, because it is chemically well defined it is easy and less costly to manufacture and to control or assure the quality of the product.

The high level of site-specificity of the wholly synthetic peptide immunogen of the present invention minimizes the generation of antibodies that are directed to irrelevant sites present on more complex enterobacterial immunogens and peptide-carrier protein immunogens. The immune response generated is focused against FAFSD B cell epitopes, and is site-specific for promiscuous Th sites so that undesirable T cell responses such as epitopic suppression are avoided. It is shown below that the present invention provides an effective method for the prevention of the adherence of *E. coli* and other enterobacteria to the bladder mucosa to confer protection against urinary tract infection.

The peptide immunogens of the present invention comprise six optimized functional FAFSD target peptides that are involved in carbohydrate recognition within the FimH molecule as the candidate "B cell target sites" for the development of a UTI vaccine (see Table 3, SEQ ID Nos: 3–8). Each of the FAFSD target peptide (SEQ ID NOS:3–8, Table 3) is a short linear or cyclized peptide and is non-immunogenic by itself. The FAFSD peptide sequences were selected to correspond to a surface-accessible site on the FimH that forms the carbohydrate-binding pocket. Cross-reactive and functional immunological analogs of the FAFSD peptides, SEQ ID NOS:3–8, may further comprise conservative substitutions, additions, deletions, or insertions of from one to about four amino acid residues provided that the peptide analogs are capable of eliciting immune responses crossreactive with the FAFSD peptides.

The conservative substitutions, additions, and insertions may be with natural or non-natural amino acids as defined hereinbelow. Cross-reactive and functional analogs also include modifications that preserve native-like conformations. As shown in Table 3, FAFSD peptide sequences SEQ ID NOS:4–8 are those modified from the native sequence by inserting or substituting a cysteine to introduce and control cyclic constraint in the peptide to ensure cross-reactivity with a native site conformation.

Other exemplary analogs include CEDYPDTITC (SEQ ID NO:86) that has a conservative insertion between positions 1 and 2 and a conservative substitution at position 5 relative to SEQ ID NO:6 and CNDYPETITDAC (SEQ ID NO:87) that has a conservative insertion between positions 10 and 11 relative to SEQ ID NO:6. Cross-reactive and functional analogs also includes peptides that have 1 to 5 additional amino acids of the mannose binding domain of FimH1 added to either terminus or in which a looped structure is substantially preserved. For example, TQIFCHNDYPETITDCYVDLA (SEQ ID NO: 88), is an analog of SEQ ID NO:6. Suitable FAFSD target peptides of the invention also include homologous fimbrial sequences taken from the corresponding region of serological variants of type 1 fimbriated uropathogenic bacteria.

Further analogues of the FAFSD target peptides of the present invention may also be identified by the use of random peptide libraries described and disclosed in Pieczenik, U.S. Pat. No. 5,866,363; Kauffman et al, U.S. Pat. No. 5,723,323; and Blume et al, U.S. Pat. No. 6,010,861, incorporated herein by reference. As described therein, a random library may be constructed by random addition of nucleotides or the random polymerization of oligonucleotides. A random library of peptides, or polypeptides expressed from a random gene library is screened with each of the antibodies generated using the FAFSD peptides according to the present invention. The peptides or polypeptides that bind to each of the antibodies to the FAFSD peptides are mimetopes of the FAFSD peptide and are useful also as analogues thereof. Analogues of FAFSD peptides, therefore, also includes such mimetopes.

To ensure functional immunogenicity, the FAFSD target peptide are designed with structural characteristics that closely resemble the conformation of the target site on the native molecule to ensure immunological cross-reactivity to the authentic target. Accordingly, cysteines have been added or substituted to provide for a loop conformation or to control a loop conformation in a FAFSD target peptide. The designed cyclic constraints mimic the natural conformation of the relevant FimH target site. In this manner a FAFSD peptide is a functional antibody target site to generate antibodies with cross-reactivity for the corresponding natural functional site on FimH.

A crucial factor affecting the functional immunogenicity of a synthetic FAFSD peptide immunogen is its presentation to the immune system by T helper cell epitopes (Th). The peptide immunogen of the present invention employs promiscuous Th epitopes for immunostimulation. Thus, the peptide immunogen of the present invention comprise a FAFSD peptide as a target for B cell interaction combined with a Th peptide to promote T helper activity.

Th epitopes useful in the present invention include those derived from foreign pathogens including but not limited to those shown in Table 1. Further, Th epitopes include idealized artificial Th and idealized artificial combinatorial Th shown in Table 2 as SEQ ID NOS:30–71. See, U.S. Pat. No. 6,025,468. The Th epitope may be modified to include functional immunological analogs, such as immune enhancing analogs, crossreactive analogs and segments thereof. Functional Th analogs include conservative substitutions, additions, deletions and insertions of from one to about 10 amino acid residues of a specific Th epitope and any other modification in accordance with the Rothbard 1, 4, 5, 8 rule, or MHC-binding motifs or any modification that does not essentially affect the Th-stimulating function of the Th epitope. A combinatorial Th library is produced simultaneously in a single solid-phase peptide synthesis in tandem with a FAFSD peptide and optionally with an invasin domain peptide as described below.

Optionally, the peptide immunogen of the present invention further comprise, as a generalized immunostimulatory element, a domain of an invasin protein from the bacteria Yersinia spp (SEQ ID NO:72). A preferred embodiment of the invasin domain (Inv) for linkage to a promiscuous Th epitope has been previously described in U.S. Pat. No.

TABLE 3

Optimized FimH Adhesin Functional Site Derived Peptides (FAFSD Peptides)

| SEQ ID NO. | Amino acid sequence | Description |
| --- | --- | --- |
| SEQ ID NO:2 | CKTANGTAIPIGGGSANVYVN-LAPVVC | aa 3–28(C)[1] |
| SEQ ID NO:3 | FACKTANGTAIPIGGGSANVYVNLA | aa 1–25 |
| SEQ ID NO:4 | FASKTCNGTAIPIGGGSANCYVNLA | aa 1–25, (C3 S3)[3], (A6 C6)[2,4], (V20 C20)[5] |
| SEQ ID NO:5 | CASKTANGTAIPC | (C)[1]aa 2–12(C)[2], (C3 S3)[3] |
| SEQ ID NO:6 | CDYPETITC | (C)[1]aa 47–53(C)[1,2] |
| SEQ ID NO:7 | CNDYPETITDC | (C)[1]aa 46–54(C)[1,2] |
| SEQ ID NO:8 | CILRQTNNYNSDDFQFVC | (C)[1]aa 130–145(C)[1,2] |

[1]cysteine added to natural sequence of C- and/or N-terminii
[2]peptide cyclized through cysteines
[3]substitution of cysteine by serine
[4]substitution of alanine by cysteine
[5]substitution of valine by cysteine 5,759,551 and is incorporated herein by reference. The Inv domain has the sequence:

Thr-Ala-Lys-Ser-Lys-Lys-Phe-Pro-Ser-Tyr-Thr-Ala-Thr-Tyr-Gln-Phe  (SEQ ID NO:72)

or an immune stimulatory homologue thereof from the corresponding region of an invasin protein in another Yersinia species. Such homologues may contain substitutions, deletions or insertions of amino acid residues to accommodate strain to strain variation, provided that the homologues retain immune stimulatory properties. The invasin domain (Inv) is attached through a spacer to the FAFSD peptide or the Th epitope peptide.

The short constrained FAFSD peptide with the proper conformation may also be immunopotentiated by chemical coupling to a carrier protein, for example, keyhole limpet hemocyanin (KLH), or by fusion through recombinant DNA expression to a carrier polypeptide, for example, the hepatitis B surface antigen. However, as discussed above, the major problem of such "FAFSD peptide-carrier" vaccine is that a large proportion of the antibodies generated are non-functional antibodies directed against the carrier protein or polypeptide with a high potential for epitopic suppression. Therefore, conjugation with a carrier protein is not preferred.

The present invention provide FAFSD peptides that are effective in generating antibodies that are cross reactive with the native FAFSD target site with minimal generation of irrelevant antibodies. The FAFSD peptide is covalently linked to promiscuous Th epitopes to evoke site-specific immunoreactivity. The antibodies generated prevent the adherence of $E.\ coli$ to the bladder mucosa to confer protection against urinary tract infection. Because the sequence of the FimH protein is conserved throughout the Enterobacteria genera, it is expected that the peptide immunogens of the present invention would be effective to prevent the adherence of other endobacteriae to the bladder mucosa to protect agains urinary tract infection of other endobacteriae.

Specific examples are provided to illustrate the various embodiments of the present invention. However, the scope of the invention is not to be limited thereby. The examples include covalently binding synthetic immunostimulatory elements to a FAFSD peptide such that potent FAFSD peptide-reactive antibodies are generated in a genetically diverse host population. The antibodies, in turn, are cross-reactive to FimH and lead to inhibition of the attachment of the FimH adhesin molecule to bladder mucosa, and protect against urinary tract infection by $E.\ coli$ and other enterobacteriae.

The Th peptide is covalently attached, with a spacer (e.g., Gly-Gly, $\epsilon$-N Lys), to either the N- or C-terminus of the target FAFSD peptide. The peptide immunogen of this invention is represented by one of the following formula:

(A)$_n$-(FAFSD peptide)-(B)$_o$-(Th)$_m$-X or (A)$_n$-(Th)$_m$-(B)$_o$-(FAFSD peptide)-X or (FAFSD peptide)-(B)$_o$-(Th)$_m$-(A)$_n$-X or (Th)$_m$-(B)$_o$-(FAFSD peptide)-(A)$_n$-X wherein
  each A is independently an amino acid or an invasin domain;
  each B is independently an amino acid or a linking group chosen from the group consisting of an amino acid, gly-gly, ($\alpha$, $\epsilon$-N)lys, Pro-Pro-Xaa-Pro-Xaa-Pro (SEQ ID NO:73); NHCH(X)CH$_2$SCH$_2$CO—, —NHCH(X)CH$_2$SCH$_2$CO($\epsilon$-N)Lys-, —NHCH(X)CH$_2$S-succinimidyl($\epsilon$-N)Lys-, and —NHCH(X)CH$_2$S-(succinimidyl)-;
  each Th comprise an amino acid sequence that constitutes a helper T cell epitope, or an immune enhancing analog or segment thereof;
  (FAFSD peptide) is a synthetic peptide B cell target site antigen selected from the group consisting of SEQ ID NOS:3–8 or a cross-reactive and immunologically functional analog thereof;
  X is an $\alpha$-COOH or $\alpha$-CONH$_2$ of an amino acid
  n is from 0 to about 10;
  m is from 1 to about 4; and
  o is from 0 to about 10.

The peptide immunogen of the present invention comprises from about 20 to about 100 amino acid residues, preferably from about 25 to about 80 amino acid residues and more preferably from about 25 to about 65 amino acid residues.

When A is an amino acid, it is a non-naturally occurring or naturally occurring amino acid. Non-naturally occurring amino acids include, but are not limited to, $\epsilon$-N lysine, $\beta$-alanine, ornithine, norleucine, norvaline, hydroxyproline, thyroxine, $\gamma$-amino butyric acid, homoserine, citrulline and the like. Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. When m is greater than one, and two or more of A are amino acids, then each amino acid may independently be the same or different. When A is Inv, it is the immune stimulatory domain from the invasin protein of a Yersinia species (SEQ ID NO:72) or a homologue thereof. Preferably, (A)$_n$, includes a spacer, e.g., Gly-Gly, $\epsilon$-N Lys, through which the Inv domain is linked to the peptide. In one preferred embodiment, (A)$_3$ is Inv, glycine and glycine, in that order, i.e., Inv-gly-gly.

B is an amino acid which can be naturally occurring or non-naturally occurring amino acids as described above. Each B is independently the same or different. B can provide a spacer, e.g., Gly-Gly, $\epsilon$-N Lys, between the promiscuous Th epitope and the FAFSD peptide. In addition to physically separating the Th epitope from the B cell epitope, i.e., the FAFSD, the presence of a spacer can disrupt any artifactual secondary structures created by the joining of the Th epitope with the FAFSD peptide. This eliminates any interference that may exist between the Th and/or B cell responses. B may also be in the form of a flexible hinge providing further separation of the Th and the FAFSD peptide. Examples of sequences encoding flexible hinges are found in the immunoglobulin heavy chain hinge region. Flexible hinge sequences are often proline rich. One particularly useful flexible hinge is provided by the sequence Pro-Pro-Xaa-Pro-Xaa-Pro (SEQ ID NO:73), where Xaa is any amino acid, preferably aspartic acid. The conformational separation provided by B permits more efficient interactions between the presented peptide immunogen and the appropriate T cells and B cells providing enhanced immune responses to the Th epitope and the antibody-eliciting epitope of the immunogen.

Th is a sequence of amino acids (natural or non-natural amino acids) that comprises a Th epitope. A Th epitope may be a continuous or discontinuous epitope. In a discontinuous Th epitope, not every amino acid of Th is necessary. A Th epitope, or an analog or segment thereof, is capable of enhancing or stimulating an immune response to the FAFSD peptide. Th epitopes that are immunodominant and promiscuous are highly and broadly reactive across animal and human populations with widely divergent MHC types (Partidos et al., 1991; U.S. Pat. No. 5,759,551). The Th domain of the subject peptides is about 10 to about 50 amino acids, preferably from about 10 to about 30 amino acids. When multiple Th epitopes are present (i.e., $m \geq 2$), each Th epitope may be the same or different. A Th segment comprises a contiguous portion of a Th epitope that is sufficient to enhance or stimulate an immune response to the FAFSD peptide (SEQ ID NOS:3–8).

The preferred peptide immunogens of this invention are the peptides containing a FAFSD peptide selected from the group consisting of SEQ ID NOS: 3–8 and a cross-reactive and functional immunological analog thereof; a spacer; a Th epitope selected from the group consisting of HBs Th (SEQ ID NO:9), HBc Th (SEQ ID NO:28), an $MV_F$ Th (SEQ ID NOS:16,17), PT Th (SEQ ID NO:10), TT Th (SEQ ID NO:18); a CT Th (SEQ ID NOS:20,29), DT Th (SEQ ID NO:21) SM Th (SEQ ID NO:24), TraT1 Th (SEQ ID NO:25), TraT2 Th 9SEQ ID NO:26) TraT3 (SEQ ID NO:27), (see Table 1), an artificial Th (e.g. SEQ ID NOS:35–37,38–39,49–50, 67), (see Table 2) or an analogue thereof. Optionally, the preferred immunogen comprises an Inv domain (SEQ ID NO:72) or a homologue thereof. The preferred peptide composition may comprise a cocktail of the peptide immunogens. The preferred peptide immunogens of the present invention may also comprise two or more novel Th epitopes with enhanced immunopotency in a broader population to provide an improved FAFSD immune response.

The peptide immunogens of this invention can be made by chemical synthesis well known to an ordinarily skilled artisan. See, for example, Fields et al., Chapter 3 in *Synthetic Peptides: A User's Guide*, ed. Grant, W. H. Freeman & Co., New York, N.Y., 1992, p. 77. The peptide immunogen can be synthesized using the automated Merrifield techniques of solid phase synthesis with the $\alpha$-$NH_2$ protected by either t-Boc or F-moc chemistry using side chain protected amino acids on, for example, an Applied Biosystems Peptide Synthesizer Model 430A or 431. Preparation of peptide constructs comprising combinatorial library peptides for Th epitopes can be accomplished by providing a mixture of alternative amino acids for coupling at a given variable position.

After complete assembly of the desired peptide immunogen, the resin is treated according to standard procedures to cleave the peptide from the resin and deblock the functional groups on the amino acid side chains. The free peptide is purified by HPLC and characterized biochemically, for example, by amino acid analysis or by sequencing. Purification and characterization methods for peptides are well known to one of ordinary skill in the art.

The immunogen of the present invention may also be polymerized. Polymerization can be accomplished for example by reaction between glutaraldehyde and the —$NH_2$ groups of the lysine residues using routine methodology. By another method, the synthetic $(A)_n$-(FAFSD peptide)-$(B)_o$-$(Th)_m$-X or $(A)_n$-$(Th)_m$-$(B)_o$-(FAFSD peptide)-X or (FAFSD peptide)-$(B)_o$-$(Th)_m$-$(A)_n$-X or $(Th)_m$-$(B)_o$-(FAFSD peptide)-$(A)_n$-X immunogen can be polymerized or co-polymerized by the addition of a cysteine to the N-terminus of the synthetic "$(A)_n$-(FAFSD peptide)-$(B)_o$-$(Th)_m$-X" or "$(A)_n$-$(Th)_m$-$(B)_o$-(FAFSD peptide)-X" or "(FAFSD peptide)-$(B)_o$-$(Th)_m$-$(A)_n$-X" or "$(Th)_m$-$(B)_o$-(FAFSD peptide)-$(A)_n$-X" immunogen. The immunogen of the present invention may also be prepared as a branched polymer by synthesis of the desired peptide construct directly onto a branched poly-lysyl core resin (Wang, et al., *Science*, 1991; 254:285–288).

Alternatively, the longer synthetic peptide immunogens can be synthesized by well known recombinant DNA techniques. Such techniques are provided in well known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The efficacy of the peptide composition of the present invention can be established by injecting an animal, for example, guinea pigs, with an immunogenic composition comprising peptides of the invention. See, Table 4, SEQ ID NOS:74–85. The humoral immune response to the FAFSD peptide is monitored. A detailed description of the procedures used is provided in the Examples.

Another aspect of this invention provides a peptide composition comprising an immunologically effective amount of one or more of the peptide immunogens of this invention in a pharmaceutically acceptable delivery system. Accordingly, the subject peptides can be formulated as a peptide composition using adjuvants, pharmaceutically-acceptable carriers or other ingredients routinely provided for the formulation of peptide compositions. Among the ingredients that can be used in this invention are adjuvants or emulsifiers including alum, incomplete Freund's adjuvant, liposyn, saponin, squalene, L121, emulsigen monophosphyryl lipid A (MPL), QS21, SEPPIC ISA51, ISA35, ISA206 and ISA 720 as well as the other efficacious adjuvants and emulsifiers. The composition may be formulated for immediate release and/ or sustained release, for induction of systemic immunity, for example, immunogen entrapment by or coadministration with microparticles. Such formulations are readily available to one of ordinary skill in the art. The immunogens of the present invention can be administered by any convenient route, such as subcutaneous, oral, intramuscular, or other parenteral or enteral route. The immunogens can be administered as a single dose or in multiple doses. A suitable immunization schedule is readily determined and available to one of ordinary skill in the art.

The peptide composition of the instant invention comprises an effective amount of one or more of the peptide immunogens of the present invention and a pharmaceutically acceptable carrier. Such a composition in a suitable dosage unit form generally contains about 0.25 μg to about 500 μg of the immunogen per kg body weight. When delivered in multiple doses, it may be conveniently divided into an appropriate amount per dosage unit. For example, an initial dose, e.g. 0.0025–0.5 mg per kg body weight; preferably 1–50 μg per kg of body weight of the peptide immunogen is to be administered by injection, preferably intramuscularly, followed by repeat (booster) doses. Dosage will depend on the age, weight and general health of the subject as is well known in the vaccine and therapeutic arts.

The immune response to synthetic FAFSD peptide immunogens can be improved by delivery through entrapment in or on biodegradable microparticles of the type described by O'Hagan et al. (*Vaccine*, 1991; 9: 768–771). The immunogens can be encapsulated with or without an adjuvant in biodegradable microparticles, to potentiate immune responses, and to provide time-controlled release for sustained or periodic responses, and for oral administration, (O'Hagan et al, 1991; Eldridge et al., *Molec Immunol*, 1991; 28: 287–294).

UTIs are a major complication among pregnant and elderly women with some estimates of the rate of bacteriuria ranging as high as 25%. Treatment of these cases has become increasingly difficult due to the emergence of multiply resistant pathogens. Recent reports have described urinary isolates of *E. coli* and *Klebsiella pneumoniae* from hospitalized patients that are resistant to all available antibiotics including β-lactams, amino glycosides, and glycopeptides. Because of this alarming situation, new approaches for the prevention and management of UTIs are clearly warranted. The use of vaccines comprising the FAFSD peptide immunogens of the present invention, that elicit antibody responses to welldefined bacterial virulence determinants such as the mannose binding sites in the adhesin of FimH, will evoke broad protective immunity in individuals predisposed to UTIs. The study described in the examples indicate that a vaccine comprising peptides representing the mannose binding sites of bacterial FimH has considerable potential in evoking broadly protective immunity against UTIs.

Specific peptide immunogens and compositions are provided in the following examples to illustrate the invention. These examples are for purpose of illustration only, and are not to be construed as limiting the scope of the invention in any manner.

EXAMPLE 1

Typical Methods to Synthesize FAFSD Peptide(s) Comprising Constructs

Peptides listed in Tables 4 (SEQ ID NOS:74–85) were synthesized individually by the Merrifield solid-phase synthesis technique on Applied Biosystems automated peptide synthesizers (Models 430, 431 and 433A) using Fmoc chemistry. Preparation of peptide constructs comprising combinatorial library Th, i.e., idealized artificial Th site termed (SEQ ID NOS:49–50), can be accomplished by providing a mixture of the desired amino acids for chemical coupling at a given position as specified in the design. After complete assembly of the desired peptide, the resin was treated according to standard procedure using trifluoroacetic acid to cleave the peptide from the resin and deblock the protecting groups on the amino acid side chains. For cyclic peptide, the cleaved peptide was dissolved in 15% DMSO in water for 48 hrs to facilitate intradisulfide bond formation between cysteines. The cleaved, extracted and washed peptides were purified by HPLC and characterized by mass spectrometry and reverse phase HPLC.

TABLE 4

| SEQ ID NOS | Description of FAPSD peptide immunogen | Amino Acid sequence |
|---|---|---|
| 74–75 | Simplified Th IS (1,4,9 Palindromic) Th[a] -εK-FAFSD (SEQ ID NO:3) | ISISEIKGVIVHKIEGILF-GG-FACKTANGTAIPIGGGSANVYVNLA<br>　　　　T　　RT　　TR　T |
| 76–77 | Simplified Th IS (1,4,9 Palindromic) Th[a] -εK-FAFSD (SEQ ID NO:4) | ISISEIKGVIVHKIEGILF-GG-FASKTCNGTAIPIGGGSANCYVNLA<br>　　　　T　　RT　　TR　T |
| 78–79 | Simplified Th IS (1,4,9 Palindromic) Th[a] -εK-FAFSD (SEQ ID NO:5) | ISISEIKGVIVHKIEGILF-GG-CASKTANGTAIPC<br>　　　　T　　RT　　TR　T |

TABLE 4-continued

| SEQ ID NOS | Description of FAPSD peptide immunogen | Amino Acid sequence |
|---|---|---|
| 80–81 | Simplified Th IS (1,4,9 Palindromic) Th[a] -εK-FAFSD (SEQ ID NO:6) | ISISEIKGVIVHKIEGILF-GG-CDYPETITC<br>  T   RT   TR  T |
| 82–83 | Simplified Th IS (1,4,9 Palindromic) Th[a] -εK-FAFSD (SEQ ID NO:7) | ISISEIKGVIVHKIEGILF-GG-CNDYPETITDC<br>  T   RT   TR  T |
| 84–85 | Simplified Th IS (1,4,9 Palindromic) Th[a] -εK-FAFSD (SEQ ID NO:8) | ISISEIKGVIVHKIEGILF-GG-CILRQTNNYNSDDFQFVC<br>  T   RT   TR  T |

[a]"Simplified Th IS (1,4,9 Palindromic) Th" is SEQ ID NOS: 49–50 (Table 2)

EXAMPLE 2

Typical Methods to Evaluate Immunogenicity of FAFSD Peptides

FAFSD peptide immunogens were evaluated on groups of guinea pigs as specified by the experimental immunization protocol outlined below and by serological assays for determination of immunogenicity.

Standard Experimental Design:

Immunogens:

(1) Individual peptide immunogen; or (2) Mixtures comprising equal molar peptide immunogens as specified in each example.

Dose: 100 μg in 0.5 mL per immunization unless otherwise specified

Route: Intramuscular unless otherwise specified

Adjuvants: Freund's Complete Adjuvant (CFA)/Incomplete

Adjuvant (IFA); or water in oil emulsions unless otherwise specified CFA/IFA groups received CFA week 0, IFA in subsequent weeks.

Dose Schedule: 0, 3, and 6 weeks or otherwise specified.

Bleed Schedule: Weeks 0, 5, 8 or otherwise specified

Species: Duncan-Hartley guinea pigs or otherwise specified

Group Size: 3 or 5 group

Assay: Specific ELISAs for the anti-peptide reactivity of each immune serum, solid phase substrate was the cyclized FAFSD peptide (SEQ ID NOS:3–8).

Blood was collected and processed into serum, and stored prior to titering by ELISA with the target antigenic peptides.

Anti-FAFSD peptide(s) antibody activities were determined by ELISAs (enzyme-linked immunosorbent assays) using 96-well flat bottom microtiter plates which were coated with the cyclized FAFSD target peptide (SEQ ID NOS:3–8) as immunosorbent. Microtiter plates were coated with FAFSD target peptide by adding 100 μL of the peptide immunogen solution to each well at a concentration of 5 μg/mL and incubating for 1 hour at 37° C. The plates were blocked by another incubation at 37° C. for 1 hour with a 3% gelatin/PBS solution. The blocked plates were then dried and used for the assay. 100 μL samples of the diluted immune sera being tested, starting with a 1:100 dilution in a sample dilution buffer and tenfold serial dilutions thereafter, were added to the peptide coated plates. The plates were incubated for 1 hour at 37° C.

The plates were washed six times with 0.05% PBS/Tween® buffer. 100 μL of horseradish peroxidase labeled goat-anti-species specific antibody was added at appropriate dilutions in conjugate dilution buffer (Phosphate buffer containing 0.5M NaCl, and normal goat serum). The plates were incubated for 1 hour at 37° C. before being washed as above. Aliquots (100 μL) of ophenylenediamine substrate solution were then added. The color was allowed to develop for 5–15 minutes before the enzymatic color reaction was stopped by the addition of 50 μL 2N $H_2SO_4$. The $A_{492nm}$ of the contents of each well was read in a plate reader. ELISA titers were calculated based on linear regression analysis of the absorbances, with cutoff $A_{492nm}$ set at 0.5. This cutoff value was rigorous as the values for diluted normal control samples run with each assay were less than 0.15.

EXAMPLE 3

Assays to Assess Anti-Sera's Immunoreactivity with Type 1 Fimbriated *E. Coli*

The functional reactivity of various FAFSD peptide-specific antisera with native type 1 fimbriae can be determined by assay for antibody-mediated inhibition of type 1 fimbriae-induced yeast cell (*Candida albicans*) agglutination. The number of type 1-fimbriated bacterial cells to be added to the test system was pre-determined by titrating the *E. coli* (ORN103(pSH2) bacteria for yeast cell agglutination activity. The lowest concentration of bacteria that produced a strong agglutination reaction was used. Twofold dilutions (20 μl) of each antibody in PBS was combined with 40 μl of 1.0% yeast suspension, into which was added 40 μl of $10^9$ CFU/ml bacteria. The mixtures of antisera, yeast and bacteria were incubated at 37° C. for 1 hour. Yeast cell agglutination inhibition was assessed visually. The decrease in aggregation can be graded from + to ++++ in comparison with those obtained with pre-immune sera and normal sera. This easy and convenient assay does not require the isolation of type 1 fimbriae from bacteria.

EXAMPLE 4

Assays to Assess Anti-Adhesive Properties of Antibodies

The reactivities of various FAFSD peptide-specific antisera can be assessed in vitro for their anti-adhesive properties by:

A. Assays for antibody mediated inhibition of the binding of type 1 fimbriated *E. coli* to mouse bladder epithelial cell lines in vitro. The ability of the various FAFSD peptide specific antisera to block bacterial binding to bladder epithelial cells is undertaken in vitro. Specifically $1\times10^8$ *E. coli* (50 µl) were preincubated with an equal volume of various concentrations of antibody for 30 min at 37° C. After which, this mixture is poured on a cover slip containing a monolayer of $1\times10^5$ bladder epithelial cells. The mixture is incubated for 1 hr. after which the monolayer is vigorously washed to remove all loosely adherent bacteria. The monolayer is fixed and stained with methylene blue. Inhibition of bacterial adherence is determined by microscopic counting of the number of adherent bacteria per 200 epithelial cells.

B. Assays for antibody mediated inhibition of type 1 fimbriated *E. coli* invasion into mouse bladder epithelial cell lines in vitro. Inhibition of invasion by the fimbriated *E. coli* into mouse bladder epithelial cells can the determined by the following assay. Briefly, the antisera are incubated at various dilutions (e.g., 1:40) with type 1 fimbriated *E. coli* for 30 min. The bacterial-antisera mixture is added to the bladder epithelial cells at a ratio of 100 bacteria to 1 cell. The resulting mixture is briefly centrifuged to promote contact and uptake. Incubate the mixture at 37° C. for 3 hours. Gentamycin is then added to the mixture to kill extracellular bacteria. The bladder cell monolayers are then solubilized with tritonX-100 at appropriate dilutions and the type 1 fimbriated *E. coli* bacteria that had been taken up by the bladder epithelial cells is measured by determining the survivors as colony forming units. Degree of inhibition of bacterial invasion is graded from + to ++++ for the various immune sera in comparison to that of a panel of preimmune and normal sera.

EXAMPLE 5

Immunogenicity and in Vitro Efficacy of Representative Synthetic Constructs as Vaccine Synthetic constructs with SEQ ID NOS:74–85 were synthesized according to Example 1 and evaluated on guinea pigs by the experimental design as described in Example 2. Functional properties of the immune sera were assessed on coded samples by Dr. Soman N. Abraham of the Department of Pathology, Duke University Medical Center, Durham N.C., using his standard assays for inhibition of type1 fimbriae-induced yeast cell aggregation, and for inhibitions of bacterial adherence to and uptake into mouse bladder epithelial cells, as described in Examples 3 and 4. As shown in Table 5, vaccine designs incorporating target peptides representing mannose binding sites on the adhesin protein of FimH were found to be highly immunogenic when attached to a representative artificial Th epitope such as the "IS (Simplified Th lib)LF Th" (SEQ ID NOS:49–50) of Table 2. All animals received three standard immunizations and high titers ($Log_{10}$ titers in the range of 2.0 to 5.0) of antibodies against the corresponding target mannose binding site peptides were elicited. Furthermore, all mannose binding site-directed immune sera recognized the bacterial fimbriae as shown by inhibition of fimbriae-induced yeast cell aggregation. The degree of inhibition of aggregation was found to be scored as + to ++++, with antisera to target SEQ ID NOS:3, 4, 5, 6, and 7 found to be more effective in inhibiting the fimbrae-induced aggregation than that of SEQ ID NO:8. All mannose binding site-directed immune sera were also found to inhibit *E. coli*-Bladder Cell Adhesin/Invasion; with antisera to target SEQ ID NOS:5, 6, 7 and 8 being more effective in such inhibition than those of SEQ ID NOS:3 and 4.

The mode of protection effected by the FimH mannose binding site-specific antibodies can be mediated through blocking and reversing the specific adherence of the challenge bacteria to the walls of the bladder, thus effectively preventing bacteria from establishing an early foothold and establishing proof of efficacy for peptide compositions of the invention.

TABLE 5

| SEQ ID NO. | Description of "IS(simplified Th lib)LF-εK-"FimH target" | Formulation | Animal No. | $Log_{10}$ Titer Anti-target peptide ELISA | Degree of Inhibition of Yeast Aggregation | Degree of Inhibition in Bladder Cell Adhesion/invasion |
|---|---|---|---|---|---|---|
| SEQ ID NOs: 74–75 | SEQ ID NO.3 | CFA/IFA | 1231 1232 1233 | 4.683 | +++ | + |
| SEQ ID NOs: 76–77 | FimH[1–3(C→S)-6(A→C)-20(V→C)-25] SEQ ID NO. 4 | CFA/IFA | 1401 1402 1403 | 4.868 | +++ | + |
| SEQ ID NOs: 78–79 | FimH[1 (F→C)-13(I→C)] SEQ ID NO. 5 | CFA/IFA | 1237 1238 1239 | >5.0 | ++++ | +++ |
| | | ISA 51 | 1407 1408 1409 | >5.0 | ++ | +++ |
| | | ISA 720 | 1425 1426 1427 | 4.706 | +++ | ++++ |

TABLE 5-continued

| SEQ ID NO. | Description of "IS(simplified Th lib)LF-εK-"FimH target" | Formulation | Animal No. | Immune Sera Reactivity in Functional Assays | | |
|---|---|---|---|---|---|---|
| | | | | Log₁₀ Titer Anti-target peptide ELISA | Degree of Inhibition of Yeast Aggregation | Degree of Inhibition in Bladder Cell Adhesion/invasion |
| SEQ ID NOs: 80–81 | (C)FimH[46–54](C) SEQ ID NO. 6 | CFA/IFA | 1405 1406 | 3.131 | +++ | +++ |
| | | ISA 720 | 1433 | 2.268 | +++ | ++++ |
| SEQ ID NOs: 82–83 | (C)FimH[47–53](C) SEQ ID NO. 7 | CFA/IFA | 1401 1402 1403 | 3.996 | ++ | ++ |
| | | ISA 51 | 1410 1411 1412 | 2.995 | ++ | ++ |
| | | ISA 720 | 1428 1429 | 2.737 | ++++ | +++ |
| SEQ ID NOs:84–85 | FimH[129 (L→C)-146(W→C)] SEQ ID NO. 8 | CFA/IFA | 1240 1241 1242 | 4.899 | + | +++ |
| | | ISA 51 | 1243 1244 1245 | 4.021 | + | +++ |
| | | ISA 51/DDA | 1246 1247 1248 | 3.715 | + | +++ |
| | | ISA 720 | 1252 1253 1254 | 3.429 | ++ | ++++ |
| Normal and preimmune sera | | | | <0.5 | – | – |

What is claimed is:

1. A FAFSD target peptide selected from the group consisting of SEQ ID NOS: 4, 6, 8.

2. A FAFSD target peptide according to claim 1 wherein the FAFSD peptide is an analogue thereof that is crossreactive with an immunologically functional for FimH of fimbriae if *E. coli* and is selected from the group consisting of SEQ ID NOs: 5, 7, 86, 87 and 88.

3. A peptide immunogen represented by the formulas (A)$_n$-(FAFSD peptide)-(B)$_o$-(Th)$_m$-X or (A)$_n$-(Th)$_m$-(B)$_o$-(FAFSD peptide)-X or (FAFSD peptide)-(B)$_o$-(Th)$_m$-(A)$_n$-X or (Th)$_m$-(B)$_o$-(FAFSD peptide)-(A)$_n$-X wherein each A is independently an amino acid or an invasin domain;

each B independently an amino acid or a chemical linker chosen from the group consisting of: amino acids, Gly-Gly, (αε-N) Lys, Pro-Pro-Xaa-Pro-Xaa-Pro (SEQ ID NO:73); NHCH(X)CH$_2$SCH$_2$CO—, —NHCH(X)CH$_2$SCH$_2$CO(ε-N )Lys-, —NHCH(X)CH$_2$S-succinimidyl(ε-N)Lys-, and —NHCH(X)CH$_2$S-(succinimidyl)-;

each Th is independently a sequence of amino acids that constitutes a helper T cell epitope, or an immune enhancing analog or segment thereof;

(FAFSD peptide) is a FAFSD target peptide selected from the group consting of SEQ ID NO:4, 6, 8; and analogue thereof that is crossreactive with and immunologically functional for FimH of fimbriae of *E. coli*;

X is α-COOH or α-CONH$_2$;

n is from 0 to about 10;

m is from 1 to about 4; and o is from 0 to about 10.

4. A peptide immunogen comprising a carrier protein covalently attached to a FAFSD target selected from the group consisting of SEQ ID NOS: 4, 6, and 8.

5. A peptide immunogen according to claim 4 wherein the FAFSD peptide is an analogue thereof that is crossreactive with and immunologically functional for FimH of fimbriae of *E. coli* and is selected from the group consisting of SEQ ID NOs: 5, 7, 86, 87 and 88.

6. A peptide immunogen of claim 4 wherein the FAFSD target peptide is cyclized.

7. A peptide immunogen of claim 5 wherein the FAFSD target peptide is cyclized.

8. A peptide immunogen of claim 3, wherein B is an amino acid selected from the group consisting of natural and unnatural amino acids.

9. A peptide immunogen of claim 4 wherein said Th is a combinational Th epitope library.

10. A peptide immunogen of claim 5 wherein said Th is a combinational Th epitope library.

11. A peptide immunogen of claim 3 wherein said Th is a combinational Th epitope library.

12. A peptide immunogen of claim 2 wherein said Th is a an amino acid sequence selected from the group consisting of SEQ ID NO:9, SEQ ID NO:10, SEQ ID NO:16, SEQ ID NO:17, SEQ ID NO:18, SEQ ID NO:20, SEQ ID NO:21, SEQ ID NO:28, SEQ ID NO:29, SEQ ID NOS:38–39, and SEQ ID NO:49–50, and SEQ ID NO:67.

13. A peptide immunogen of claim 4 wherein said Th has an amino acid sesquence selected from the group consisting of SEQ ID NO:9, SEQ ID NO:10, SEQ ID NO:16, SEQ ID NO:17, SEQ ID NO:18, SEQ ID NO:20, SEQ ID NO:21, SEQ ID NO:28, SEQ ID NO:29, SEQ ID NOS:38–39, and SEQ ID NOS:49–50, and SEQ ID NO:67.

14. A peptide immunogen of claim 5 wherein said Th has an amino acid sesquence selected from the group consisting of SEQ ID NO:9, SEQ ID NO:10, SEQ ID NO:16, SEQ ID NO:17, SEQ ID NO:18, SEQ ID NO:20, SEQ ID NO:21, SEQ ID NO:28, SEQ ID NO:29, SEQ ID NOS:38–39, and SEQ ID NOS:49–50, and SEQ ID NO:67.

15. A peptide immunogen of claim 3 wherein said Th has an amino acid sesquence selected from the group consisting of SEQ ID NO:9, SEQ ID NO:10, SEQ ID NO:16, SEQ ID NO:17, SEQ ID NO:18, SEQ ID NO:20, SEQ ID NO:21, SEQ ID NO:28, SEQ ID NO:29, SEQ ID NOS:38–39, and SEQ ID NOS:49–50, and SEQ ID NO:67.

16. A peptide immunogen of claim 3 wherein said peptide immunogen has an amino acid sequence selected from the group consisting of SEQ ID NOs:74, 75, 76, 77, 78, 79, 80, 81, 82, 83, 84 and 85.

17. A peptide immunogen of claim 3 wherein at least one A is an invasin domain.

18. A peptide immunogen of claim 3 wherein n is 3, and $(A)_3$ is (invasin domain)-Gly-Gly.

19. A peptide immunogen of claim 17 or claim 18 wherein said invasin domain has the amino acid sequence of SEQ ID NO:72.

20. A peptide immunogen according of claim 3 wherein the FAFSD peptide is an analogue that is crossreactive with and immunologically functional for FimH of fimgriae of *E. coli* selected from the group consisting of SEQ ID NOs: 5, 7, 86, 87 and 88.

21. A polymer of at least two FAFSD peptides of claim 1 cross-linked by a bifunnctional crosslinking agent.

22. A polymer of aat least two FAFSD peptide of claim 2 cross-linked by a bifunctional crosslinking agent.

23. A polymer of least two FAFSD peptide immunogens of claim 4 cross-linked by a bifunctional crosslinking agent.

24. A polymer of least two FAFSD peptide immunogens of claim 5 cross-linked by a bifunctional crosslinking agent.

25. A pharmaceutical composition comprising an immunologically effective amount of a target peptide immunogen of any one of claims 4, 5, 6, 7, 3, 8, 9, 10, 11, 12, 13, 14, 15, 16, 17, or 18, and a pharmaceutically acceptable vaccine delivery vehicle.

26. A pharmaceutically composition of claim 25, wherein said immunologically effective amount of said peptide or peptide conjugate is about 0.25 µg to about 1 mg per kilogram body weight per dose.

27. A pharmaceutically composition comprising an immunologically effective amount of a target peptide immunogen of claim 19, and a pharmaceutically acceptable vaccine delivery vehicle.

28. A pharmaceutically composition of claim 27, wherein said immunologically effective amount of said peptide or peptide conjugate is about 0.25 µg to about 1 mg per kilogram body weight per dose.

* * * * *